United States Patent

Celebuski

Patent Number: 5,247,099
Date of Patent: Sep. 21, 1993

[54] PROCESS FOR SYNTHESIS OF 7-HYDROXY COUMARINS HAVING SUBSTITUTIONS IN THE 4-POSITION

[75] Inventor: Joseph E. Celebuski, Gurnee, Ill.

[73] Assignee: Abbott Laboratories, Abbott Park, Ill.

[21] Appl. No.: 703,448

[22] Filed: May 21, 1991

Related U.S. Application Data

[62] Division of Ser. No. 394,052, Aug. 17, 1989, abandoned.

[51] Int. Cl.$^5$ ............................................. C07D 311/16
[52] U.S. Cl. ........................................................ 549/289
[58] Field of Search .......................................... 549/289

[56] References Cited

U.S. PATENT DOCUMENTS 3,933,859  1/1976  Kaiser et al. ................... 549/289

FOREIGN PATENT DOCUMENTS 0255343  3/1988  Fed. Rep. of Germany .
0455954  1/1975  U.S.S.R. .
1014053  12/1965  United Kingdom .

OTHER PUBLICATIONS

Brewster/McEven *Organic Chemistry* 3rd Ed. 1961 pp. 345-347.

*Primary Examiner*—C. Warren Ivy
*Assistant Examiner*—A. Owens
*Attorney, Agent, or Firm*—Thomas D. Brainard

[57] ABSTRACT

A process for synthesis of a compound of the formula:

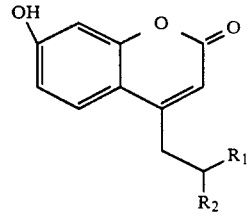

said process comprising the steps of (a) reacting 4-bromomethyl-7-methoxy coumarin with a malonic ester under conditions sufficient to achieve condensation of the ester to give the monoalkylated (2-bis(carbalkoxy)-2-$R_1$-1-ethyl) derivative; (b) removing one of the carbalkoxy groups from the product of step (a); (c) demethylation of the product of step (b) to give the 7-hydroxycoumarin compound; and (d) chemically modifying the remaining ester to yield a desired $R_2$.

9 Claims, No Drawings

PROCESS FOR SYNTHESIS OF 7-HYDROXY COUMARINS HAVING SUBSTITUTIONS IN THE 4-POSITION

This is a divisional of application Ser. No. 07/394,052, filed Aug. 17, 1989, now abandoned.

BACKGROUND OF THE INVENTION

This invention relates to fluorescent 7-hydroxy coumarin compounds with substitutions in the 4 position having a length greater than one carbon atom. The compounds thus are derivatives of 4-methylumbelliferone (7-hydroxy-4-methyl coumarin, or 4-MU), the detectable label used in the $IM_x$ ® instrument assays (Abbott Laboratories, Abbott Park, Ill.).

A number of fluorometric labels are known to one of ordinary skill in the art. However, for compatibility reasons, applicants desired a fluorophore label that had electronic properties substantially similar to the 4-MU utilized in the $IM_x$ ® instrument. Otherwise, the label might fluoresce at a wavelength the instrument could not detect absent special filters and the like. A label optimized to the existing instrument was necessary.

The search began for a coumarin or umbelliferone nucleus that had an activated or activatable tether that could be coupled to a desired molecule. Such a tether to a coumarin nucleus had been obtained in the past by a Pechmann condensation to give either a 4-position methyl group or a 3-position alkyl substitution on the coumarin [H. V. Pechmann and C. Duisberg, Chem. Ber. 16, 2119 1883)]:

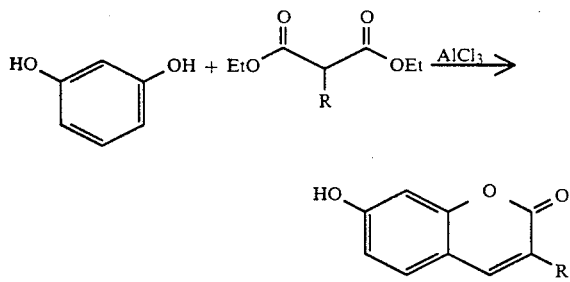

Where R represents the activatable tether.

The 4-methyl product does not provide an activatable tether group. The effect of 3-position substitution on electronic structure in coumarins is shown in the $^{13}C$ NMR spectra complied by Parmar and Boll [*Mag. Res. Chem.*, 26, 430–433 (1988)]. If R of the product above is H, the $^{13}C$ NMR chemical shift of C-3 is 110 ppm; while if R is $CH_2COOEt$, C-3 resonates at 115 ppm. This means that the relative electron density on C-3 has decreased upon alkyl substitution, disturbing the electronic structure of the coumarin nucleus. Thus, the Pechmann condensation was not useful since it did not produce 4-substituted materials, exclusive of having substitution at the 3-position, and since a compound having no substituent at the 3-position was desired because of the need for substantially similar electronic properties as 4-MU.

SUMMARY OF THE INVENTION

In one aspect, the invention relates to a compound of the formula:

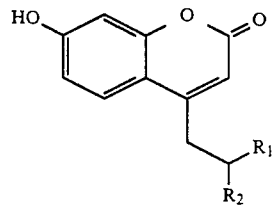

wherein $R_1$ is selected from the group consisting of H, —G—OZ, —G—SZ, —G—NHY, —SZ, —NHY, substituted phenyl, and substituted or unsubstituted alkyl of the general formula —G—$CH_3$, where G represents an alkylene chain having from 1 to about 25 carbon atoms, and Z and Y represent protecting groups; and wherein $R_2$ is selected from the group consisting of H, —J—OH, —J—SH, —J—$NH_2$, —COOH, —J—OTs, —J—X, —SH, —$NH_2$, —COOR′, and substituted or unsubstituted alkyl of the general formula —J—$CH_3$, where J represents an alkylene chain having from 1 to about 10 carbon atoms, X represents a halide, and R′ represents an alkylene chain having from 1 to about 10 carbon atoms.

In another aspect, the invention relates to a process of synthesis for the compounds described above. The steps of the synthesis comprise:

a) reacting 4-bromomethyl-7-methoxycourmarin with a monoalkylated ($R_1$) malonic ester under conditions sufficient to achieve condensation of the ester to give the monoalkylated (2-bis(carbalkoxy)-1-ethyl) derivative;

b) removing one of the carbalkoxy groups from the product of step a);

c) demethylation of the product of step b) to give the 7-hydroxycoumarin compound; and d) chemically modifying the remaining ester to yield a desired $R_2$ Preferably, step b) is performed according to the process of Krapcho in the presence of NaCl and DMSO at high temperatures. It is also preferred that step c) is performed by reacting ethanethol (EtSH) with the product of step b) at 0° C. in the presence of $AlCl_3$ and dichloromethane.

Finally, the invention also comprises a method of using the compounds described above. The 7-hydroxy-4-methyl coumarins are known to fluoresce. By conjugating the compounds to a biological macromolecule, the presence of absence of the macromolecule can be quantified. For example, a method of using compounds according to the invention comprises:

a) coupling the compound to a biological macromolecule to be used in a reaction of interest; and b) determining the amount of macromolecule by measuring the fluorescence of the compound.

Preferably, the compounds according to the invention are conjugated to a member of a specific binding pair, such as an antibody of antigen for determination in an immunoassay. They may also be conjugated to oligonucleotides and used in PCR or other hybridization assays.

DETAILED DESCRIPTION OF THE INVENTION

The invention comprises compositions of matter, processes of synthesis and methods of use for the compounds.

Compounds:

In one aspect, the invention relates to compounds having the general formula:

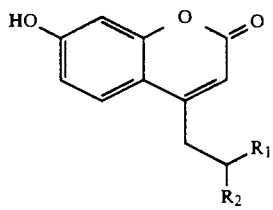

$R_1$ is selected from the group consisting of H, —G—OZ, —G—SZ, —G—NHY, —SZ, —NHY, substituted or unsubstituted phenyl, and substituted or unsubstituted alkyl of the general formula —G—$CH_3$, where G represents an alkylene chain having from 1 to about 25 carbon atoms, and Z and Y represent protecting groups. $R_2$ is selected from the group consisting of H, —J—OH, —J—SH, —J—$NH_2$, —COOH, —J—OTs, —J—X, —SH, —$NH_2$, —COOR', and substituted or unsubstituted alkyl of the general formula —J—$CH_3$, where J represents an alkylene chain having from 1 to about 10 carbon atoms, X represents a halide, and R' represents an alkylene chain having from 1 to about 10 carbon atoms.

Arbitrarily, $R_1$ derives from the central, monoalkylated $R_1$ of the malonic ester; while $R_2$ is converted from the COOEt end chain of the ester. $R_1$ can be selected from any of the groups listed above, although H is preferred. Other $R_1$ groups may require protecting groups to enable them to withstand the ensuing reactions. As used herein, "protecting group" refers to any group that can be attached to a functional moiety permitting it to withstand future reaction conditions without destroying the function; and which later can be removed or substituted to give back the functional group. For example, if alcohol or thiol groups are used, a protective group Z is used. In the case of alcohols, Z may be t-butyldimethylsilyl of tetrahydropyran; while for thiols, a preferred Z is triphenylmethyl. Protective group Y is similarly required for amino substituents. In this case, acetyl is a preferred protecting group. It is to be understood, of course, that other protecting groups are known in the art, and are obvious extension falling within the scope of the invention.

$R_2$ can be a greater number of groups since it is converted from the COOEt ester after the other reactions are completed. Conventional organic chemistry methods can place almost any group in the $R_2$ position, although there is little practical reason why some groups would be made. The preferred group will be dictated by the linking moiety present on the biological macromolecule of interest (see below). For example, if the macromolecule contains a primary amine, it is preferred that $R_2$ be (or be converted to) a N-hydroxysuccinimide ester. Other preferred $R_2$ groups are given in Table 1 below. A tosyl group, Ts, may also be created at $R_2$ and is useful as an intermediate to create other $R_2$ groups as shown in the Examples.

As used herein, "alkylene" refers to any straight or branched chain spacer groups containing less than 50 carbon atoms, including but not limited to, —$CH_2$—, —CH($CH_3$)—, —CH($C_2H_5$)—, —CH($CH_3$)$CH_2$—, —($CH_2$)$_3$—, and the like. The length of the alkylene chain is preferably short to enhance solubility, to avoid steric problems, and to be readily available commercially. Ideally, the alkylene chain G should be from 1 to about 10 carbon atoms long, while the alkylene chain J should be from 1 to about 5 carbon atoms long. In either case, the alkylene chain may be substituted.

"Aryl" refers to substituents having ring structures. For solubility reasons, phenyl or substituted phenyl is preferred over larger aryl groups.

Both aryl and alkylene substituents at the $R_1$ positions may be substituted. As used herein, "substituted" refers to the presence of moieties covalently bonded to the aryl or alkylene groups, including, but not limited to, halide (especially Br and Ci), nitro, lower alkoxy (having from 1–6 carbon atoms, especially methoxy and ethoxy), lower alkyl (having from 1–6 carbon atoms, especially methyl and ethyl), hydroxy, and amino (protecting group may be required). Subject to the limits of organic chemistry, the substituting groups may be placed anywhere, and in any number, on the alkylene or phenyl substituent.

It should be recalled that the object of the invention was to put a tether group in the 4 position of the coumarin nucleus. Therefore, if $R_1$ is H, it is pointless to convert $R_2$ to H or alkyl since there would then be no functional group to serve as a tether. It is important to the invention that at least one of $R_1$ and $R_2$ provide a functional group that is, or can be activated to be, reactive with a biological macromolecule or a linker as described below.

The compounds of the present invention find utility as fluorophores. Specifically, the side chains in the 4 position enable the compounds to be covalently coupled to other molecules through conventional chemistries, without affecting the electron configurations that are responsible for this fluorometric properties. For example, the 7-hydroxy-2-oxo-2H-1-benzopyran-4-propionic acid was synthesized for the purpose of covalently labeling biological macromolecules such as oligonucleotide primers. An example of how the compounds are so used can be found in copending application Ser. No. 07/394,051, filed Aug. 17, 1989 which is incorporated herein by reference. The labeled macromolecules can then be detected by any fluorometric procedure, such as on an $IM_x$ ® instrument, without recourse to enzymatic signal amplification.

The compounds can be also be used as dye markers at the 5' end of an oligonucleotide for sequencing purposes.

Process of Synthesis:

The compounds of the present invention can be chemically synthesized in 3 or more steps starting the from 4-bromomethyl-7-methoxycoumarin 1 (Aldrich Chemical Co., Milwaukee, Wis.). The compounds were prepared as shown below. Generally speaking, malonic ester displacement of the bromide in 1, in the presence of NaH, afforded monoalkylated 2 according to the following reaction:

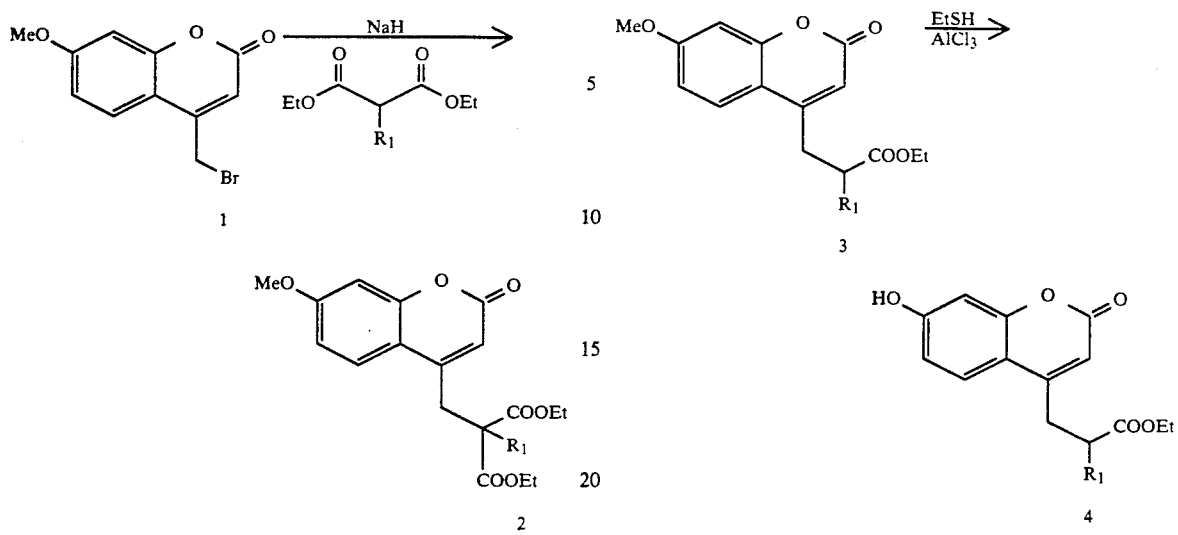

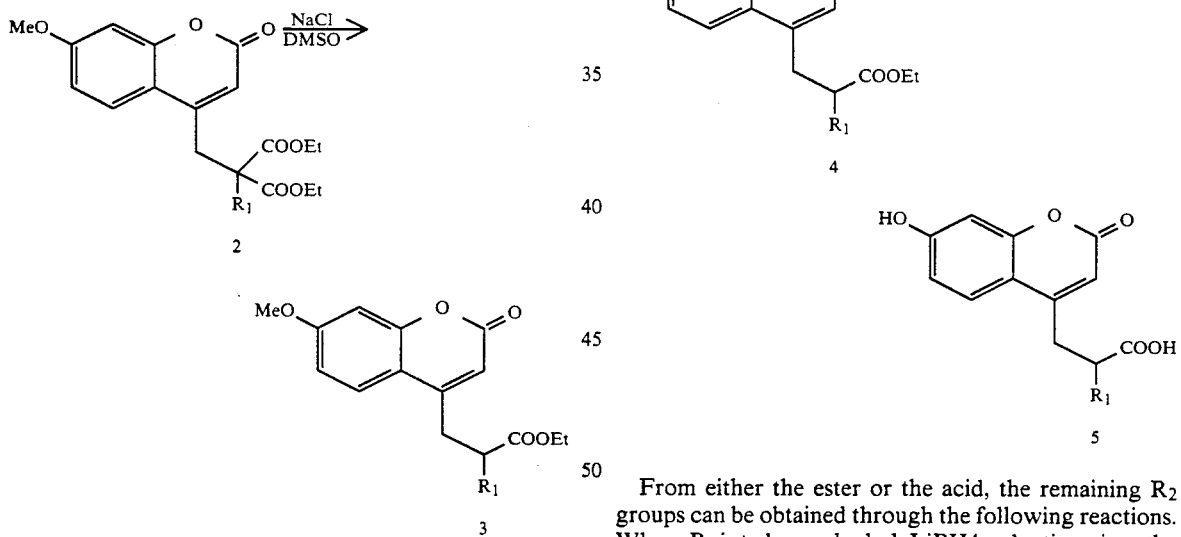

Krapcho decarbalkoxylation [Krapcho, A. P.; Weimaster, J. F.; Eldridge, J. M.; Jahngen, Jr., E. G. E.; Lovey, A. J.; Stephens, W. D. *J. Org. Chem.* (1978) 43: 138-147] removed one of the two ester groups to give 3 in good yield. The reaction is best carried out at high temperatures using NaCl as follows:

Demethylation of 3 to give the 7-hydroxycoumarin was accomplished under the conditions of Fujita as described in [Node, et al *J. Org. Chem.* (1980) 45: 4275-4277]. Briefly, the conditions involve a strong Lewis acid, AlCl3, and ethane thiol (EtSH) as a weak Lewis base, a source of protons, and a soft nucleophile. After several other methods {including BBr3, [McOmie, et al. *Tetrahedron* (1968) 24: 2289-2292]; Me3SiI, [Ho, et al, *Angew, Chem.* (1976) 88: 847]; and NaSEt [Feutrill, et al. *Tetrahedron Letters* (1970) 161: 327-328]} failed, the conditions of Fujita finally effected demethylation to give 4, albeit in only low yields.

The ester is among the claimed R2 groups. To arrive at the other R2 groups, conventional organic chemistry can be used, directly from the ester or from other intermediate groups. For example, saponification of 4 gave the acid 5 as shown below.

From either the ester or the acid, the remaining R2 groups can be obtained through the following reactions. Where R2 is to be an alcohol, LiBH4 reduction gives the desired product. The alcohol hydroxyl can then be converted to either the thiol or the amino through the intermediate hydroxy tosylate. The ester may also be reduced to the aldehyde using diisobutylaluminum hydride (DIBAL, Aldrich Chemical Co.). Longer alkylene chains can be synthesized from the aldehyde using an appropriate Wittig or Wadsworth/Emmons reagent.

Methods of Use:

Finally, the invention also comprises a method of using the compounds described above. The 7-hydroxy-4-methyl coumarins are known to fluoresce. By conjugating the compounds to a biological macromolecule, the presence or absence of the macromolecule can be quantified. For example, compounds according to the invention may be conjugated to antibodies for determination in an immunoassay. They may also be conjugated to oligonucleotides and used in PCR or other nucleic acid hybridization assays.

The conjugation is generally carried out by activating the fluorophore with a reactive group. In the case of a carboxyl $R_2$ to be reacted with a primary amine on a target macromolecule, the preferred activator is N-hydroxysuccinimide ester. Other activating groups are known in the art for use with the various $R_2$ groups and various target macromolecule linking moieties. Table 1 below is a nonexhaustive listing of some exemplary target moieties, likely $R_2$ groups and useful activators. In some cases, the conjugation is best performed using a linker or spacer molecule. The linker may be heterobifunctional or homobifunctional depending on the circumstances. The correct linker can also be determined by one of ordinary skill in the art.

| Target Moiety (on biomolecule) | Linker | Preferred $R_2$ Group | Activator |
|---|---|---|---|
| amine | none | carboxyl | NHS-ester |
| amine | maleimide | thiol | none (stable linkage) |
| amine | thiol | thiol | none (easily reversible linkage) |
| carboxyl | none | amine | (carbodiimide) |
| vicinal diol | (oxidation) | amine | (cyanoborohydride reduction after linkage) |
| thiol | none | amine | maleimide (stable linkage) |
| thiol | none | thiol | none (easily reversible linkage) |
| hydroxyl | (convert to tosyl) | amine | none |
| hydroxyl | (convert to phosphate ester) | hydroxyl | none |

The invention will now be further described by way of Examples.

EXAMPLES

EXAMPLE 1

Synthesis of 4-(2-carboxy-1-ethyl)-7-hydroxy-2-oxo-2H-1-Benzopyran

Throughout this example, R represents Hydrogen.

A. materials and Methods

Chemical reagents were purchased from Aldrich. Proton NMR spectra were obtained at 300 MHz on a General Electric QE-300 spectrometer, referenced to TMS internal standard in ppm (δ). Coupling constants are given in hertz. Mass Spectra were obtained using direct chemical ionization on a Kratos MS 50 instrument. Amino modifier II was purchased from Clontech Laboratories (Palo Alto, Calif.) TLC analyses were done using 250 μm Analtech silica gel plates. Flash column chromatographies were run with EM Kieselgel-60 (70–230 mesh). Spectral and elemental analyses were performed by the Analytical Research Department, Abbott Laboratories.

B. Synthesis of 4-(2-bis(carbethoxy)-1-ethyl)-7-methoxy-2-oxo-2H-1-Benzopyran (2)

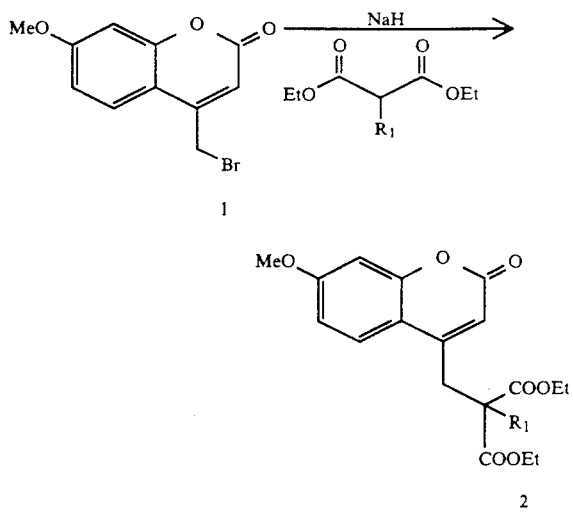

To a suspension of 240 mg of 60% NaH mineral oil dispersion (6 mmol) in 10 mL of DMF was added 961 μL (6 mmol) of diethyl malonate. After the foaming subsided and the suspension cleared to a solution, 1346 mg (5 mmol) of 4-bromomethyl-7-methoxycoumarin was added all at once. After stirring for 4 h at room temperature, the DMF was stripped off, and the residue partitioned between 0.01 M HCl/hexane. The organic phase was concentrated and vacuum dried, then as much as possible was taken up into 4 mL of 50/50 EtOAc/hexane. Flash chromatography gave 670 mg of 2 as a white solid, 49%.

Analysis gave:

1H NMR (CDCl$_3$) δ7.56 (d, 1 H, J=8.8), 6.88 (dd, 1 H, J=2.6, 8.8), 6.84 (br s, 1H), 4.23 (q, 2 H, J=7.2), 4.22 (q, 2 H, J=7.2), 3.88 (s, 3 H), 3.74 (t, 1 H, J=7.4), 3.36 (dd, 2 H, J=1.1, 7.4), 1.27 (t, 6 H, J=7.4)

MS m/z 349 (100, M+H)

IR (film, cm−1) 1715 (vs), 1614 (vs)

Anal. (C$_{18}$H$_{20}$O$_7$) C, H.

C. Synthesis of 4-(2-carbethoxy-1-ethyl)-7-methoxy-2-oxo-2H-1-Benzopyran (3)

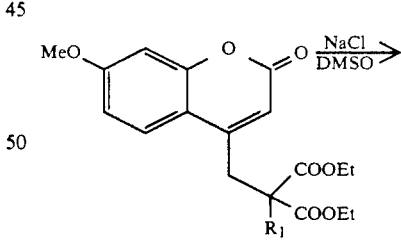

To a solution of 44.8 mg (0.13 mmol) of 2 in 6 mL of DMSO was added 15 mg of NaCoI, followed by 4.6 mL of water. The reaction was stirred in an oil bath at 180° C. for 2.5 h, and was cooled to room temperature. After addition of 45 mL of water to the reaction mixture, the resultant emulsion was extracted with 2×40 mL EtOAc. The organic phase was concentrated by rotary evaporation, and was vacuum dried. After uptake into 3 mL of 25% EtOAc in hexane, flash chromatography using the same solvent system gave 31.4 mg of 3, 88%.

Analysis gave:

1H NMR (CDCl3) δ7.55 (d, 1H, j=8.8), 6.88 (dd, 1H, J=2.6, 8.8), 6.83 (d, 1H, J=2.6), 6.13 (t, 1H, J=1.1), 4.19 (q, 2H, J=7), 3.88 (s, 3H), 3.06 (t, 2H, J=8), 2.71 (t, 2H, J=8), 1.28 (t, 3H, J=7)

MS 277 (100, M+H)

IR (film, cm−1) 1730 (vs), 1612 (vs)

Anal. ($C_{15}H_{16}O_5$) C, H.

D. Synthesis of 4-(2-carbethoxy-1-ethyl)-7-hydroxy-2-oxo-2H-1-Benzopyran (4)

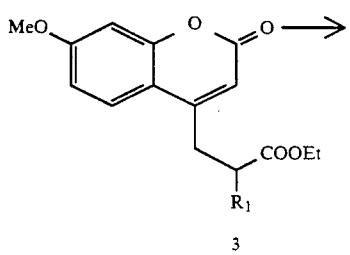

3

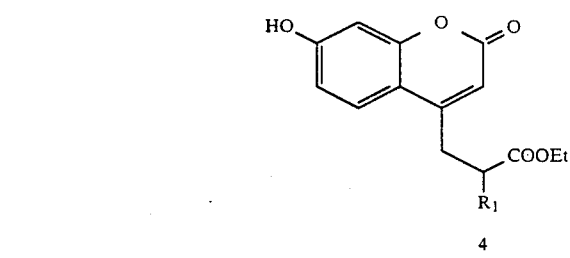

4

To a suspension of 726 mg (5.4 mmol) of AlCl3 in 10 mL of dichloromethane at 0° C. was added 4 mL of EtSH. The suspension became a clear solution within seconds. Then, 298 mg (1.08 mmol) of 3 in 4 mL of dichloromethane was added, turning the yellow solution red in color. The ice bath was removed, and the reaction stirred to room temperature for 3 h. The solvents were removed in vacuo, and the residue thoroughly vacuum dried. The residue was extracted into EtOAc as much as possible, then the extract was flash chromatographed using 30/70 EtOAc/hexane. The long- and short-wave UV active band gave 76.7 mg (27%) of 4.

Analysis gave:

1H NMR (CDCl3) δ7.5 (d, 1H, J=8.5), J=8.5), 6.9 (d, 1H, J=2.6), 6.85 (dd, 1H, J=8.5, 2.6), 6.1 (br s, 1H, 4.18 (q, 2H, J=7.4), 3.08 (br, t, 2H, J=7), 2.71 (br t, 2H, J=7), 1.28 (t, 3H, J=7.4)

MS 263 (M+H)

IR (Film, cm−1) 3280 (s, br), 1730 (vs), 1693 (vs), 1608 (vs), 1565 (s)

Anal. ($C_{14}H_{14}O_5$) C,H.

E. Synthesis of 4-(2-carboxy-1-ethyl)-7-hydroxy-2-oxo-2H-1-Benzopyran (5)

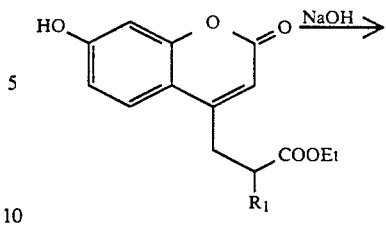

4

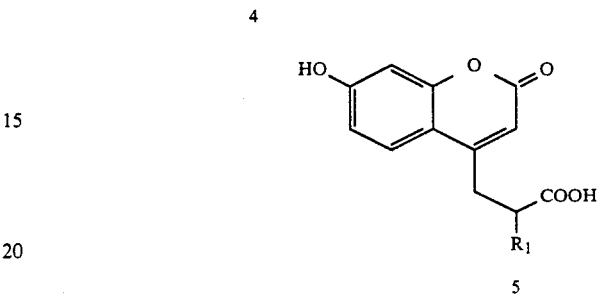

5

A 36.7 mg sample of ester 4 was suspended into 10 mL of water, and 25 mL of 50% aqueous NaOH was added. The resultant solution was stirred at room temperature for 4 h. TLC analysis (30/70 EtOAc/hexane) after this time showed that no starting material remained. The mixture was acidified using 1 mL of 1 M HCl. A precipitate formed upon acidification, and the white solid was left to deposit for 1 h. After the solid was filtered off and thoroughly washed with 1 M HCl, it was vacuum dried to give 14.1 mg (43%) of analytically pure 5.

Analysis gave:

1H NMR (NaOD/D2O) δ7.5 (d, 1H, J=8.8), 6.74 (dd, 1H, J=2.2, 8.8), 6.53 (d, 1H, J=2.2), 5.97 (br s, 1H), 2.91 (t, 2H, J=7.4), 2.5 (t, 2H, J=7.4)

MS (FAB, H2O) 235 (M+H)

IR (KBr, cm−1) 3440 (s, br), 1710 (vs), 1611 (vs), 1568 (vs), 1400 (s)

Anal. ($C_{12}H_{10}O_5$) C, H.

F. Synthesis of 4-(2-carboxy-1-ethyl)-7-hydroxy-2-oxo-2H-1-Benzopyran, N-hydroxy succinimide ester (6).

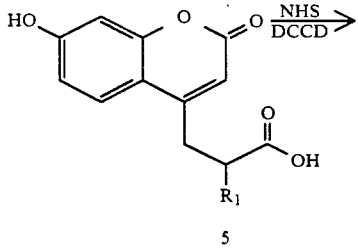

5

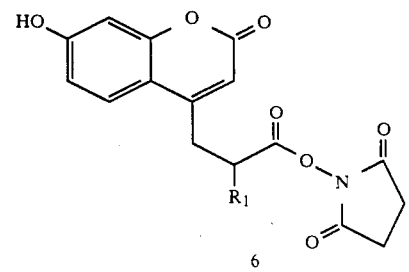

6

To a suspension of 6.4 mg (27.3 mmol) of 5 in 6 mL of MeCN was added 4.7 mg (41 mmol) of N-hydroxysuccinimide, 8.4 mg (41 mmol) of dicyclohexylcarbodiimide (DCCD) and 2 mg of 4,4-dimethylaminopyridine. The reaction was stirred at room temperature for 24 h, and the solvent was removed in vacuo. The residue was taken up into 750 μL of DMF, and coupled directly with oligonucleotide.

The coupling and use of this product are described in more detail in copending application Ser. No. 07/394,051 filed Aug. 17, 1989, which has been incorporated herein by reference.

EXAMPLE 2

Synthesis of 4-(2-carboxy-2-$R_1$-1-ethyl)-7-hydroxy-2-oxo-2H-1-Benzopyran

Example 1 is repeated with $R_1$ group s according to Table 2.

TABLE 2

$R_1$ group
—$CH_3$
—$CH_2CH_3$
—$CH_2CH_2$-O-t-butyldimethylsilyl
—$CH_2CH_2$-NH-acetyl
—NH-acetyl

EXAMPLE 3

Synthesis of Alcoholic $R_2$ Group

Compound (4) from Example 1 is modified to contain an alcoholic $R_2$ group (—$CH_2OH$) by reducing the ester with $LiBH_4$ under conditions cited by Brown in: H. C. Brown, *Hydroboration*, p. 245, Benjamin, N.Y., N.Y. (1962).

EXAMPLE 4

Synthesis of Thiol $R_2$ Group

The compound from Example 3 is modified to contain a thiol $R_2$ group (—$CH_2SH$) by conversion using the tosylate under conditions of Price and Stacy in: *Organic Synthesis Collective* vol. 3, p. 86 (1955).

EXAMPLE 5

Synthesis of Amine $R_2$ Group

The compound from Example 3 is modified to contain an amino $R_2$ group (—$CH_2NH_2$) by conversion using the tosylate under conditions of a Gabriel synthesis of primary amines, wherein the tosylate is displaced by sodium phthalimide. The phthalimide is then removed with hydrazine to give the primary amine.

The above examples serve to illustrate the invention and should not be construed as limiting the scope of the invention. Rather, the scope of the invention is limited only by the appended claims.

What is claimed is:

1. A process for synthesis of a compound of the formula:

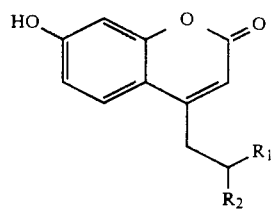

wherein $R_1$ is selected from the group consisting of H, —G—OZ, —G—NHY, —SZ, —NHY, substituted phenyl, and substituted or unsubstituted alkyl of the general formula —G—$CH_3$, where G represents an alkylene chain having from 1 to about 25 carbon atoms, and Z and Y represent protecting groups; and wherein $R_2$ is selected from the group consisting of H, —J—OH, —J—SH, —J—$NH_2$, —COOH, —J—$OT_3$, —J—X, —SH, —$NH_2$, —COOR', and substituted or unsubstituted alkyl of the general formula —J—$CH_3$, where J represents an alkylene chain having from 1 to about 10 carbon atoms, X represents a halide, and R' represents an alkylene chain having from 1 to about 10 carbon atoms; said process comprising the steps of:

a) reacting 4-bromomethyl-7-methoxycoumarin with a malonic ester under conditions sufficient to achieve condensation of the ester to give the (2-bis(carbalkoxy)-2-$R_1$-1-ethyl) coumarin derivative;

b) removing one of the carbalkoxy groups from the product of step a);

c) demethylation of the product of step b) according to the Fujita process in the presence of a strong Lewis acid and a weak nucleophilic Lewis base to give the 7-hydroxycoumarin compound; and d) chemically modifying the remaining carbalkoxy ester to yield a desired $R_2$.

2. A process according to claim 1 wherein step b) is performed according to the process of Krapcho.

3. A process according to claim 1 wherein step b) is performed in the presence of NaCl and DMSO at high temperatures.

4. A process according to claim 1 wherein step c) is performed by reacting EtSH with the product of step b) at 0° C. in the presence of $AlCl_3$.

5. A process according to claim 1 wherein step d) comprises saponification of the remaining ester to a carboxylic acid.

6. A process according to claim 1 wherein step d) comprises modifying the remaining ester to an amino group.

7. A process according to claim 1 wherein step d) comprises modifying the remaining ester to a hydroxyl group.

8. A process according to claim 1 wherein step d) comprises a Hofmann degradation.

9. A process according to claim 1 wherein step d) comprises modifying the remaining ester to convert it to a member selected from the group consisting of H, —J—OH, —J—SH, —J—$NH_2$, —COOH, —J—OTs, —J—X, —SH, —$NH_2$, —COOR', and substituted or unsubstituted alkyl of the general formula —J—$CH_3$, where J represents an alkylene chain having from 1 to about 10 carbon atoms, X represents a halide, and R' represents an alkylene chain having from 1 to about 10 carbon atoms.

* * * * *